US00PP26207P3

(12) United States Plant Patent
Zaiger et al.

(10) Patent No.: US PP26,207 P3
(45) Date of Patent: Dec. 15, 2015

(54) INTERSPECIFIC TREE NAMED 'BELLA RED'

(50) Latin Name: ***Interspecific Prunus* species**
Varietal Denomination: Bella Red

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 135 days.

(21) Appl. No.: 13/998,687

(22) Filed: Nov. 25, 2013

(65) Prior Publication Data

US 2015/0150168 P1 May 28, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

*Primary Examiner* — Keith O. Robinson

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with vigorous, upright growth.
2. Regular and productive bearer of medium to large size fruit.
3. Fruit with very good flavor and eating quality.
4. Firm fruit with good packing and shipping quality.
5. Fruit with an average Brix of 19.0°, with a good balance between acid and sugar.
6. Fruit with attractive red skin and flesh color.

1 Drawing Sheet

Botanical designation: Interspecific *Prunus* species.
Variety denomination: 'BELLA RED'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Bella Jewel' Interspecific (U.S. Plant Pat. No. 23,106) and our proprietary non-patented interspecific varieties '34M562', '288LF477', '9Z38A', '254LV124', '178LM86' and '305LN566'.

STATEMENT REGARDING FEDERALLY SPONSORED RESEARCH AND DEVELOPMENT

Not applicable.

ORIGIN OF THE VARIETY

The new and distinct variety of interspecific tree was originated by us from crosses of the following species; *Prunus salicina*, (*Prunus salicina*×*Prunus armeniaca*), (*Prunus persica*×*Prunus armeniaca*), (*Prunus salicina*×*Prunus avium*) and *Prunus armeniaca*. The interspecific tree was developed by us in our experimental orchard located near Modesto, Calif. from a first generation cross between our proprietary non-patented interspecific selections with field identification numbers '34M562' and '254LV124'. The non-patented interspecific seed parent (34M562) originated as a first generation seedling from the cross of our proprietary non-patented interspecific seedling selections '288LF477' and '9Z38A'. The non-patented interspecific pollen parent (254LV124) originated from crosses of our proprietary non-patented interspecific seedlings '178LM86' and '305LN566'. A large number of these first generation seedlings were budded onto older established trees of 'Nemaguard' Rootstock (non-patented) to enhance earlier fruit production for evaluation. Under close and careful observation we recognized the desirable tree and fruit characteristics of the present seedling and selected it in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree [Plum, PlumCot, Peachcot, Plumcherry and Apricot] is of large size, vigorous, upright growth and is a regular and productive bearer of medium to large size, dark red flesh fruit with very good flavor and eating quality. The fruit is further characterized by having firm flesh, an attractive dark red skin color with a good balance between acid and sugar. In comparison to its seed parent (34M562) interspecific (non-patented) the fruit of the new variety has dark red flesh compared to yellow and is approximately 36 days later in maturity. In comparison to its pollen parent (254LV124) interspecific (non-patented) the fruit of the new variety has darker red skin color and is approximately 23 days later in maturity. In comparison to the commercial variety 'Bella Jewel' Interspecific (U.S. Plant Pat. No. 23,106) the fruit of the new variety is approximately 55 days later in maturity.

DESCRIPTION OF THE PHOTOGRAPH

The accompanying color photographic illustration shows typical specimens of the foliage and fruit of the present new interspecific variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color published in 1958.

Tree:

*Size.*—Large, usually pruned to 3 to 3.5 meters in height and width for economical harvesting of fruit. Size varies with different cultural practices and climatic conditions.

*Vigor.*—Vigorous, tree growth of approximately 1.5 to 2 meters in height the first growing season. Varies with soil type, fertility of soil and climatic conditions.

*Form.*—Upright, usually pruned to vase shape.

*Branching habit.*—Upright, crotch angle approximately 35°, increases with heavy crop load.

*Productivity.*—Productive, thinning and spacing of fruit necessary for desired market size. Fruit set varies with climatic conditions during bloom time.

*Bearer.*—Regular, has had adequate fruit set 3 consecutive years. No alternate bearing observed.

*Fertility.*—Self sterile, pollinator required.

*Density.*—Medium dense, usually pruned to vase shape to allow more sunlight to center of tree to enhance fruit color and health of fruit spurs.

*Hardiness.*—Hardy in all stone fruit growing areas of California. Tree grown in USDA Hardiness Zone 9. Winter chilling requirement approximately 850 hours at or below 45° F.

Trunk:

*Size.*—Large. Average circumference 40.8 cm at 25.4 cm above ground on a 5 year old-tree.

*Stocky.*—Medium stocky.

*Texture.*—Medium shaggy, roughness increases with age.

*Color.*—Varies from 10YR 4/2 to 2.5Y 3/2.

Branches:

*Size.*—Medium. Average circumference 9.1 cm at 1.2 meters above ground on a 5 year old tree. Crotch angle approximately 35°, increases with heavy crop load.

*Surface texture.*—New growth relatively smooth. Mature growth medium rough, roughness increases with age.

*Lenticels.*—Average number 41 in a 25.8 square cm area. Average length 3.2 mm. Average width 1.5 mm. Color varies from 2.5Y 6/8 to 2.5Y 5/6.

*Color.*—New growth varies from 5GY 5/6 to 5GY 5/8. Mature growth varies from 2.5Y 6/8 to 2.5Y 5/6, varies with age of growth.

Leaves:

*Size.*—Medium. Average length 86.7 mm. Average width 35.4 mm.

*Form.*—Oblanceolate.

*Apex.*—Acuminate.

*Base.*—Cuneate.

*Margin.*—Serrate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Average length 11.9 mm. Average width 1.6 mm. Longitudinally grooved. Surface — light pubescence. Strength of petiole — medium. Color varies from 2.5GY 7/6 to 5GY 5/6.

*Glands.*—Type — globose. Size — small to medium. Average length 1.1 mm. Average diameter 0.6 mm. Average number 2, varies from 1 to 2. Located primarily on the base of the leaf blade and upper portion of the petiole. Color varies from 2.5GY 7/6 to 5GY 4/6.

*Stipules.*—Present. Average length 8.2 mm. Edges — pectinate. Color 5GY 5/8.

*Color.*—Upper surface varies from 5GY 4/4 to 7.5GY 4/4. Lower surface varies from 5GY 5/6 to 5GY 6/4. Midvein color varies from 2.5GY 7/4 to 2.5GY 7/2.

Flower buds:

*Size.*—Small to medium. Average length 9.6 mm. Average diameter 5.2 mm.

*Hardiness.*—Hardy with respect to California winters.

*Form.*—Conical, becoming elongated just before opening.

*Pedicel.*—Average length 7.1 mm. Average width 0.5 mm. Color varies from 2.5GY 6/8 to 5GY 7/8. Surface glabrous.

*Color.*—N 9.5/(white).

*Number of buds per spur.*—Varies from 11 to 18, average number 14. Varies with age of spur.

Flowers:

*Blooming period.*—Date of First Bloom Feb. 20, 2013. Date of Petal Fall Mar. 2, 2013, varies slightly with climatic conditions.

*Size.*—Medium to large. Average height 11.1 mm. Average diameter 20.9 mm.

*Petals.*—Normally 5, alternately arranged to sepals. Size — medium to large. Average length 10.6 mm. Average width 8.5 mm. Petal apex — rounded. Petal base — truncated. Form — elliptical. Arrangement — free. Margin — sinuate. Color N 9.5/(white). Both upper and lower surfaces glabrous.

*Sepals.*—Normally 5, alternately arranged to petals. Size — small. Average length 2.8 mm. Average width 2.5 mm. Sepal apex rounded to triangular. Shape — triangular. Margin — entire. Color — upper surface varies from 5GY 6/8 to 5GY 5/6. Lower surface varies from 5GY 6/8 to 5GY 5/8. Both upper and lower surfaces glabrous.

*Stamens.*—Average number per flower 29. Average filament length 8.1 mm. On average, the stamens are above the height of the petals. Filament color N 9.5/(white). Anther color varies from 5Y 8/8 to 5Y 8/10.

*Pollen.*—Self sterile, pollinator required. Color varies from 5Y 7/8 to 5Y 7/10.

*Pistil.*—Number — normally one. Average length 7.8 mm. Position of stigma an average of 2.5 mm below anthers. Surface pubescent. Color varies from 2.5GY 9/4 to 2.5GY 8/6.

*Fragrance.*—Heavy aroma.

*Color.*—N 9.5/(white).

*Number flowers per flower bud.*—Varies from 1 to 3, average number 2.

*Pedicel.*—Average length 9.4 mm. Average width 0.6 mm. Color varies from 2.5GY 6/8 to 5GY 7/8. Surface — glabrous.

Fruit:

*Maturity when described.*—Firm ripe and ready for consumption.

*Date of first picking.*—Aug. 6, 2013.

*Date of last picking.*—Aug. 16, 2013, varies slightly with climatic conditions.

*Size.*—Medium to large. Average diameter axially 65.4 mm. Average transversely in suture plane 61.1 mm. Average weight 125.0 grams, varies slightly with fertility of the soil, amount of thinning and climatic conditions.

*Form.*—Globose to slightly elongated.

*Suture.*—Slightly lipped, extends from base to apex.

*Ventral surface.*—Slightly lipped.

*Apex.*—Varies from rounded to slight tip.

*Base.*—Flat.

*Stem cavity.*—Rounded to slightly elongated in suture plane. Average depth 5.0 mm. Average diameter 3.9 mm.

Stem:

*Size.*—Medium. Average length 14.7 mm. Average diameter 3.9 mm.

*Color.*—Varies from 2.5GY 6/8 to 2.5GY 4/6.

Flesh:

*Ripens.*—Evenly.

*Texture.*—Firm, meaty.

*Fibers.*—Few, small, tender.

*Firmness.*—Firm, having good handling and shipping quality.

*Aroma.*—Slight.

*Amydgalin.*—Undetected.

*Eating quality.*—Very good.

*Flavor.*—Very good, good balance between acid and sugar.

*Juice.*—Moderate amount, enhances flavor.

*Acidity.*—Not available.

*Brix.*—Average Brix 19.0°, varies slightly with amount of fruit per tree and climatic conditions.

*Color.*—Varies from 5R 4/10 to 7.5R 3/10.

*Pit cavity.*—Average length 24.0 mm. Average width 17.0 mm. Average depth 5.9 mm. Color varies from 5R 2/4 to 7.5R 2/4.

Skin:

*Thickness.*—Medium.

*Surface.*—Smooth.

*Pubescence.*—Moderate amount, very short.

*Bloom.*—Heavy, completely covered.

*Tendency to crack.*—None.

*Color.*—Ground color varies from 5Y 5/8 to 7.5Y 5/8. Overspread with 5R 2/2 to 7.5R 2/2.

*Tenacity.*—Tenacious to flesh.

*Astringency.*—Undetected.

Stone:

*Type.*—Clingstone, medium adherence to flesh.

*Size.*—Medium. Average length 23.9 mm. Average width 15.6 mm. Average thickness 9.7 mm.

*Form.*—Ovoid.

*Base.*—Slightly pointed.

*Apex.*—Pointed. Average length 2.0 mm.

*Surface.*—Lightly pitted throughout, a short groove on each side of suture plane extending from base to apex.

*Sides.*—Unequal, one side extending slightly further from the suture plane.

*Ridges.*—Large wing extending from base toward apex.

*Tendency to split.*—None.

*Color.*—Varies from 2.5YR 6/8 to 5YR 6/8 when dry.

Kernel:

*Size.*—Small. Average length 13.7 mm. Average width 7.4 mm. Average depth 4.7 mm.

*Form.*—Ovoid.

*Viability.*—Viable, complete embryo development.

*Skin color.*—Varies from 5Y 9/6 to 7.5Y 9/4.

Use: Dessert.

*Market.*—Local and long distance.

Keeping quality: Good, held firm in cold storage for 3 weeks at 38° to 42° F. without internal breakdown of flesh or appreciable loss of flavor.

Shipping quality: Good, minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

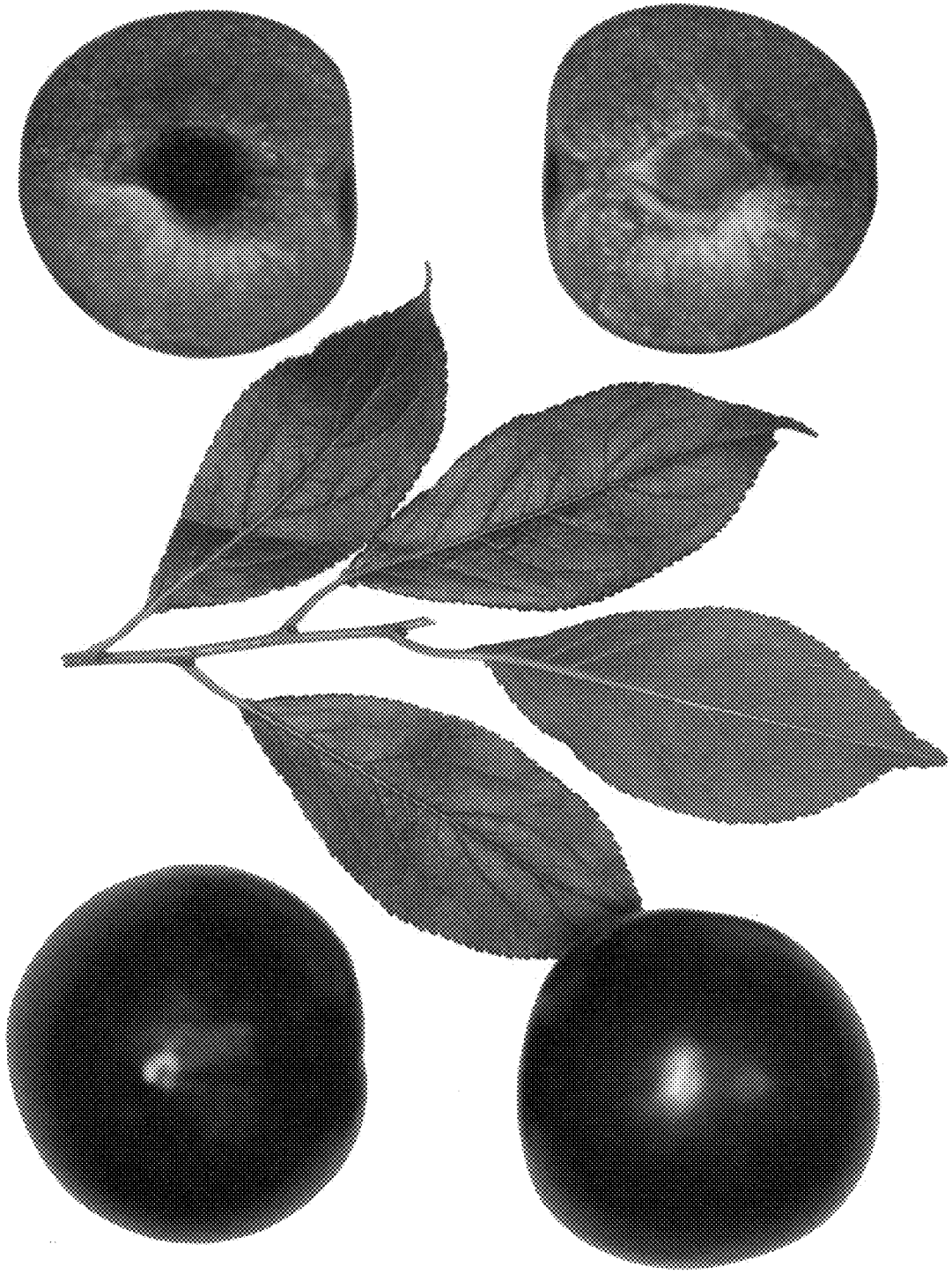

* * * * *